(12) United States Patent
Shim et al.

(10) Patent No.: US 10,794,885 B2
(45) Date of Patent: Oct. 6, 2020

(54) GAS SENSOR CONTROLLER

(71) Applicant: ALPHA M.O.S, Toulouse (FR)

(72) Inventors: Chang-Hyun Shim, Fourquevaux (FR); Jean-Christophe Mifsud, Goudourville (FR); François Loubet, Avignonet-Lauragais (FR)

(73) Assignee: ALPHA M.O.S., Toulouse (FR)

( * ) Notice: Subject to any disclaimer, the term of this patent is extended or adjusted under 35 U.S.C. 154(b) by 204 days.

(21) Appl. No.: 15/772,841

(22) PCT Filed: Nov. 2, 2016

(86) PCT No.: PCT/EP2016/076395
§ 371 (c)(1),
(2) Date: May 2, 2018

(87) PCT Pub. No.: WO2017/076882
PCT Pub. Date: May 11, 2017

(65) Prior Publication Data
US 2018/0238846 A1    Aug. 23, 2018

(30) Foreign Application Priority Data
Nov. 2, 2015   (EP) .................................... 15306745

(51) Int. Cl.
*G01N 27/12*   (2006.01)
*G01N 33/00*   (2006.01)
*G01N 33/02*   (2006.01)

(52) U.S. Cl.
CPC ....... *G01N 33/0031* (2013.01); *G01N 27/124* (2013.01); *G01N 27/128* (2013.01);
(Continued)

(58) Field of Classification Search
CPC ................... G01N 27/00–26; G01N 33/00–14
See application file for complete search history.

(56) References Cited

U.S. PATENT DOCUMENTS 4,703,646 A  *  11/1987  Muller ............... G01N 27/4141
                                                         338/34
6,496,742 B1    12/2002  Labreche
(Continued)

FOREIGN PATENT DOCUMENTS

DE      10245947 A1 *  4/2004  ......... G01N 33/0013
DE      10245947 A1    4/2004
(Continued)

OTHER PUBLICATIONS

International Search Report for PCT/EP2016/076395, dated Jan. 23, 2017.
(Continued)

*Primary Examiner* — Nguyen Q. Ha
(74) *Attorney, Agent, or Firm* — Meagher Emanuel Laks Goldberg & Liao, LLP

(57) ABSTRACT

An olfactometer or "electronic nose" is able to vary a plurality of operating parameters during a test cycle in parallel, in accordance with a measurement protocol. This measurement protocol, and correspondingly the operating parameters to be varied, the values to be set for those parameters, and the timing of the variation in these values is tailored to most effectively distinguish between likely candidates in a particular testing scenario. A characterisation library is then used to match the results of the measurement protocol to the best target in the characterisation library. Test protocols and/or characterisation libraries may be downloaded from a remote server on demand, and certain activities may be carried out either locally or remotely.

13 Claims, 13 Drawing Sheets

(52) U.S. Cl.
CPC ..... *G01N 33/0001* (2013.01); *G01N 33/0062* (2013.01); *G01N 33/02* (2013.01)

(56) References Cited

U.S. PATENT DOCUMENTS

| | | |
|---|---|---|
| 8,265,881 B1 | 9/2012 | Lakhotia |
| 10,197,519 B2 * | 2/2019 | Lakhotia ................ G01N 27/12 |
| 2008/0046195 A1 | 2/2008 | Labreche |
| 2012/0143515 A1 | 6/2012 | Norman et al. |
| 2014/0105790 A1 | 4/2014 | Gaudon et al. |

FOREIGN PATENT DOCUMENTS

| | | | |
|---|---|---|---|
| EP | 2533037 A1 | 12/2012 | |
| JP | 2010506150 A | 2/2010 | |
| KR | 20140074269 A | 6/2014 | |
| WO | WO-2019135459 A1 * | 7/2019 | ............. G01N 27/12 |

OTHER PUBLICATIONS

International Preliminary Report on Patentability for PCT/EP2016/076395, dated Mar. 23, 2018.
Chi-Hwan Han et al "Catalytic combustion type hydrogen gas sensor using TiO2 and UV-LED" published in Sensors and Actuators B 125 (2007) 224-228.
E. Comini et al "Light enhanced gas sensing properties of indium oxide and tin dioxide sensors" published in Sensors and Actuators B 65 _2000. 260-263.
English translation of Korean Office Action issued in application KR 10-2018-7014468, dated Oct. 24, 2019.

* cited by examiner

Prior Art

GAS SENSOR CONTROLLER

FIELD OF THE INVENTION

The present invention relates to the field of gas sensors and, more particularly, to gas sensors of the chemoresistor type, including Metal Oxide Sensors, and other sensors responding to different gas compositions for example by changes in electrical characteristics such as impedance, capacitance, reactance, etc.

BACKGROUND OF THE INVENTION

Gas sensors are used in many applications, notably in situations where it is desired to detect or recognize a particular gas and in situations where it is desired to determine the composition of a gas mixture. In the present text, unless the context demands otherwise; the expression "gas" will be used to designate both a specific gas species and a mixture of different gaseous species, and the general expression "characterization" will be used to designate both the process of recognizing or detecting a particular gas and the process of determining the composition of a gas. It is to be understood that references in this text to a "gas sample" generally include references to any gas which is presented to the gas sensor (whether as a discrete sample or by exposing the sensor to an ambient gaseous medium).

Gas sensors have been developed using different sensing technologies, including chemoresistor type gas sensors, such as those based on semi-conducting metal-oxides.

FIG. 1 is a cross-sectional view which illustrates, schematically, the basic structure of a first prior art semi-conducting metal-oxide type gas sensor.

As shown in FIG. 1, a semi-conducting metal-oxide type gas sensor 11 has a sensing layer 12 made of semi-conducting metal-oxide provided on an insulating layer 13 supported on a base 14. When the sensor 11 is exposed to a gas, gas particles 17 may become adsorbed on the surface of the sensing layer 12, and oxidation-reduction reactions may occur, leading to a change in the impedance (conductance, capacitance, inductance or plural of these parameters) of the sensing layer 12. This change of impedance is measured using a pair of measuring electrodes 15 and heater 16 disposed on the rear side of the base 14. Often the measurement is made by applying a potential difference across the measurement electrodes and monitoring how the impedance presented by the sensing layer changes.

In recent years semi-conducting metal-oxide type gas sensors having a "micro-hotplate" structure have been developed.

FIG. 2 is a cross-sectional view which illustrates, schematically, the general structure of a prior art semi-conducting metal-oxide type gas sensor having a micro-hotplate structure.

It will be seen from FIG. 2 that the base 24 of the sensor 21 has a hollowed-out portion 28 so that the sensing layer 22 is no longer positioned in registration with a thick portion of the base 24. Accordingly, the heater 26 which is used to heat the sensing layer 22 only needs to heat a reduced mass of material (including a relatively thin supporting membrane 29), which reduces the power consumed by the gas sensor as well as enabling the temperature of the sensing layer 22 to be increased rapidly (thus reducing the time necessary for making a measurement and reducing the time necessary for cleaning the sensing layer). Moreover, this rapid heating causes less damage to the material forming the sensing layer.

FIG. 3 illustrates a prior art sensor having a first type of micro-hotplate architecture.

In the sensor 30 of FIG. 3, the sensing layer 32 is formed on an insulating layer 33 which, in turn, overlies the base 34. Conductors 38 lead out from the measuring electrodes and heater to make contact with electrode pads 39 provided on the base 34. Additional wiring (not shown) connects the electrode pads to further circuitry, notably a source of current for the heater, and circuitry for processing the signals measured by the measurement electrodes. The sensor 30 of FIG. 3 has a "closed" type of architecture in which the base 34 has a continuous surface supporting the insulating layer 33.

FIG. 4 illustrates a prior art sensors having a second type of micro-hotplate, with a suspended architecture.

The sensor illustrated in FIG. 4 has a "suspended" type of structure in which the base 44 has a frame-type shape with a central opening 47 and the sensing layer 42 and its insulating layer 43 are suspended over the opening.

Typically, the measurements obtained from a single semi-conducting metal-oxide gas sensor element on its own are insufficient to enable a gas to be identified with a sufficient degree of certainty, because the selectivity of such sensor elements tends to be low. Accordingly, conventionally these sensing elements are used in arrays of multiple sensing elements disposed side-by-side, and each element in the array has a different material forming its sensing layer. The set of measurements obtained from the whole array forms a cloud of data points which can be processed using statistical techniques so as to determine whether or not a given gas is present and/or to determine what is the composition of the gas mixture that has been presented to the array. The set of measurements can be considered to represent a kind of fingerprint that is characteristic of the nature of the gaseous species present in the gas under analysis and their concentrations.

FIG. 5 shows conventional sensor system. In order for an "electronic nose" device to assess and identify a wide range of different chemical signatures, it is usual to arrange a number of sensor devices such as those described with reference to FIGS. 1, 2, 3 and 4 in an array. A shown in FIG. 5, there are provided three chambers 52, 53 and 54, each containing a plurality of sensors 521. The three chambers 52, 53 and 54, are connected via conduits 512, 513 respectively. A sample for analysis is injected at injector port 511, where it mixes in a controlled manner with synthetic air provided at port 510, in flow meter 55. This synthetic air acts as a carrier, carrying the sample through each of the chambers, past each sensor, and finally out of an exhaust port 514. Typically, the sensors 521 will be of different types, or configured differently, so as to react differently to different sample compositions. By collating the response of each sensor to a given sample, the system can compile a "fingerprint" of the sample, which can then be compared to a library of known "fingerprints" to identify the closest match, and thereby the most plausible sample composition.

It is a drawback of the sensor array described with reference to FIG. 5 that it is inherently bulky—the more competent a device, the more sensors it may have, and the more elaborate the arrangement of chambers and conduits required to ensure proper exposure so the sample of each sensor.

Meanwhile, there is a desire to develop compact sensor systems offering functionality comparable with that of the conventional sensor system of FIG. 5, in a package consistent with incorporation in hand held user devices.

"Handbook of Machine Olfaction: Electronic Nose technology" by Tim C Pearce et al. edited by John Wiley & Sons, 24 Jan. 2006 provides an introduction to the technical background in the field of the invention.

The articles "Catalytic combustion type hydrogen gas sensor using TiO2 and UV-LED" by Chi-Hwan Han et al published in Sensors and Actuators B 125 (2007) 224-228 and "Light enhanced gas sensing properties of indium oxide and tin dioxide sensors" by E. Comini et al published in Sensors and Actuators B 65_2000.260-263 may be consulted for further information concerning the state of the art.

Patent publications DE10245947 and US2014105790 are further referenced herewith.

SUMMARY OF THE INVENTION

In a first aspect there is provided a system for characterizing a gas, comprising a gas sensor and a controller, where the controller is adapted to modify two or more operating conditions of the gas sensor during a measurement cycle. The measurement cycle starts with an initial reading from the gas sensor and ends with a final reading from the gas sensor, and comprises a number of measurements sufficient to characterize the gas.

The modification of a plurality of operating conditions during a measurement cycle provides richer measurements supporting better discrimination between target characterisations, whilst permitting a limited overall system size.

According to a development of the first aspect, the system further comprises a memory, and the controller is further adapted to compare the readings received from the gas sensor throughout the measurement cycle with a plurality of target characterizations stored in the memory. Each target characterization is associated with a respective category, and the controller classifies the gas in the category of whichever candidate measured characterizations most closely matches the readings.

The definition of target characterisations keyed to the readings provided in accordance with the first aspect capitalises on their enriched character to automatically provide a more accurate characterisation of the gas.

According to a further development of the first aspect the system further comprises a memory, and the controller is adapted to modify the first and second operating conditions to values specified in a measurement protocol stored in that memory.

The memory of the preceding aspects may of course be one and the same. Programmed implementation of modifications to the operating conditions of the gas sensor improves the precision and facility of multiple changes to operating conditions, and further improves characterisation of the gas.

According to a further development of the first aspect the controller is adapted to initiate the measurement cycle, to modify the two or more operating conditions and to record the measurements at times specified in the measurement protocol.

Programmed implementation of modifications to the operating conditions of the gas sensor improves the precision and facility of multiple changes to operating conditions, and further improves characterisation of the gas.

According to a further development of the first aspect the system further comprises a communications interface, permitting communication with a remote processor, and is further adapted to transmit the readings received from the gas sensor throughout the measurement cycle to a remote processor for comparison with a plurality of candidate measured characterizations.

The possibility of having processing carried out remotely reduces processing effort for a user device, and reduces the need for storage capacity for numerous test protocols and characterisation libraries.

According to a further development of the first aspect the system comprises an ultra violet light source arranged so as to illuminate a reactive surface of the gas sensor. The ultra violet light source is coupled to the controller such that the controller can modulate the intensity or the wavelength of said light source, and the intensity of the light source is one of the operating conditions of the gas sensor.

Modulating the intensity or wavelength of Ultraviolet radiation can have a strong effect in modifying the reaction of the gas sensor to different gases, and as such augments the effects of the multiple modulations of the gas sensor during a measurement cycle.

According to a further development of the first aspect the system comprises a heat source arranged so as to heat a reactive surface of the gas sensor. The heat source is coupled to the controller such that the controller can modulate the intensity of the heat source, and wherein the intensity of said heat source is one of the operating conditions of the gas sensor.

Modulating the temperature can have a strong effect in modifying the reaction of the gas sensor to different gases, and as such augments the effects of the multiple modulations of the gas sensor during a measurement cycle.

According to a further development of the first aspect the system comprises a voltage source powering the gas sensor. The voltage source is coupled to the controller such that the controller can modulate the voltage output of the voltage source, and wherein the voltage of the voltage source is one of the operating conditions of the gas sensor because chemical potential due to electrical potential generated by the voltage source is a factor to control the adsorption process on/in sensing material. For example, a bias voltage provided to RS in a form of pulse can be one of examples to control the chemical potential in a transit response.

According to a further development of the first aspect the system comprises a chemical filter situated so as to control access of the gas to the gas sensor. This chemical filter comprises a heater coupled to the controller such that the controller can modulate the temperature of output of the chemical filter, and wherein the temperature of said chemical filter source is one of the operating conditions of the gas sensor.

Modulating the reaction of the gas sensor to different gases by means of a variable chemical filter provides an additional means for varying the behaviour of the system during a measurement cycle, and thereby achieving further improved discrimination and accuracy.

In a second aspect there is provided a method of characterizing a gas comprising the steps of setting initial operating conditions for a gas sensor, initiating a measurement cycle by taking a first reading from the gas sensor, modifying a first operating condition of the gas sensor at a first predefined time, modifying a second operating condition of the gas sensor at a second predefined time, and terminating the measurement cycle with a final reading from said gas sensor, wherein said steps are defined in a measurement protocol.

The modification of a plurality of operating conditions during a measurement cycle provides richer measurements supporting better discrimination between target characterisations.

According to a further development of the second aspect the method comprises the further step of comparing the readings from the gas sensor with a plurality of target characterizations, each target characterization being associated with a respective category, and classifying the gas in the category of whichever candidate measured characterizations most closely matches the readings.

The definition of target characterisations keyed to the readings provided in accordance with the first aspect capitalises on their enriched character to automatically provide a more accurate characterisation of the gas.

According to a further development of the second aspect the method comprises the further steps of transmitting the readings to a remote processor for comparison with a plurality of candidate measured characterizations, and receiving the characterization from said remote processor.

The possibility of having processing carried out remotely reduces processing effort for a user device, and reduces the need for storage capacity for numerous test protocols and characterisation libraries.

According to a further development of the second aspect further steps of generating said measurement protocol by determining at what times during a measurement cycle readings should be taken, and what values should be set for said first operating condition and said second operating condition to discriminate most clearly between said target characterizations.

Programmed implementation of modifications to the operating conditions of the gas sensor improves the precision and facility of multiple changes to operating conditions, and further improves characterisation of the gas.

According to a third aspect there is provided a method of generating a measurement protocol by determining at what times during a measurement cycle readings should be taken, and what values should be set for said first operating condition and said second operating condition to discriminate most clearly between said target characterizations.

Programmed implementation of modifications to the operating conditions of the gas sensor improves the precision and facility of multiple changes to operating conditions, and further improves characterisation of the gas.

According to a fourth aspect there is provided a method of defining a set of target characterisations in a characterisation library corresponding to a particular sample type, said method comprising the steps of determining for a plurality of possible classifications of the sample of that type which sample characterisations arising from a specified measurement protocol would support the most discriminating matching between that classification and the sample characterisation.

Predetermined mappings between sample types, measurement protocol and classification library make the most of the possibilities of the test apparatus and give an improved prospect of accurate and specific results.

According to a fifth aspect there is provided a computer program adapted to implement the steps any of the second, third, or fourth aspects.

According to a sixth aspect there is a computer readable medium incorporating the computer program of the fifth aspect.

BRIEF DESCRIPTION OF THE DRAWINGS

The above and other features, advantages and applications of the present invention will become more apparent from the following description of embodiments thereof, given by way of non-limiting examples, and the accompanying drawings, in which.

DETAILED DESCRIPTION OF CERTAIN EMBODIMENTS

Figure 5:
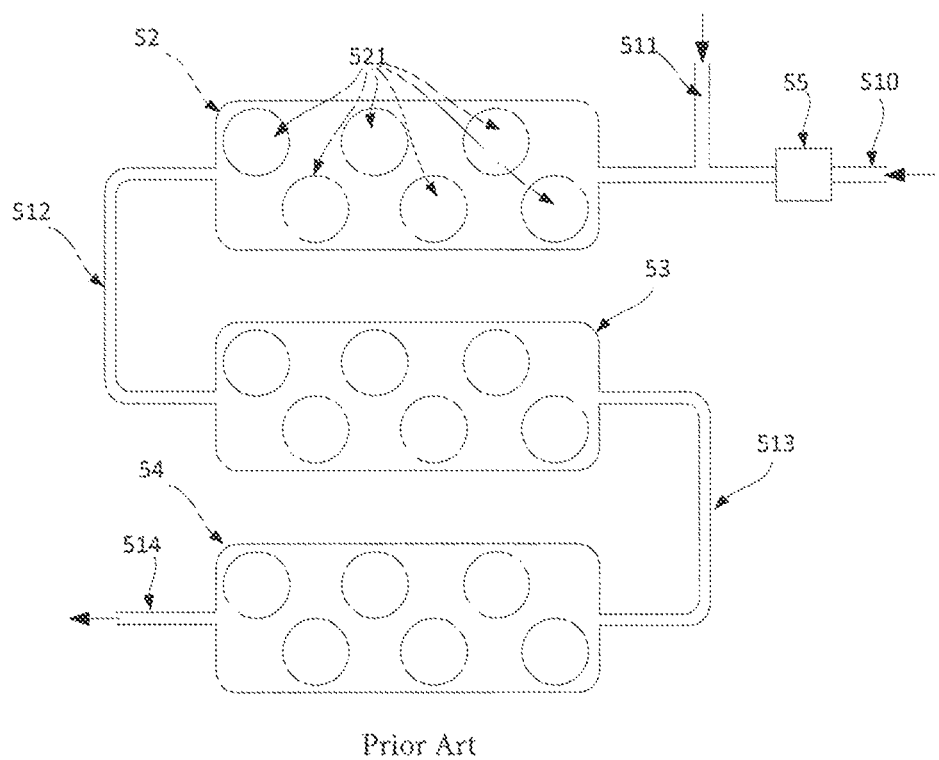
FIG. 5 shows a sensor system as known in the prior art.

In a sensor system as described with respect to FIG. 5, each sensor will generally have fixed operating conditions during a test cycle.

Figure 6:
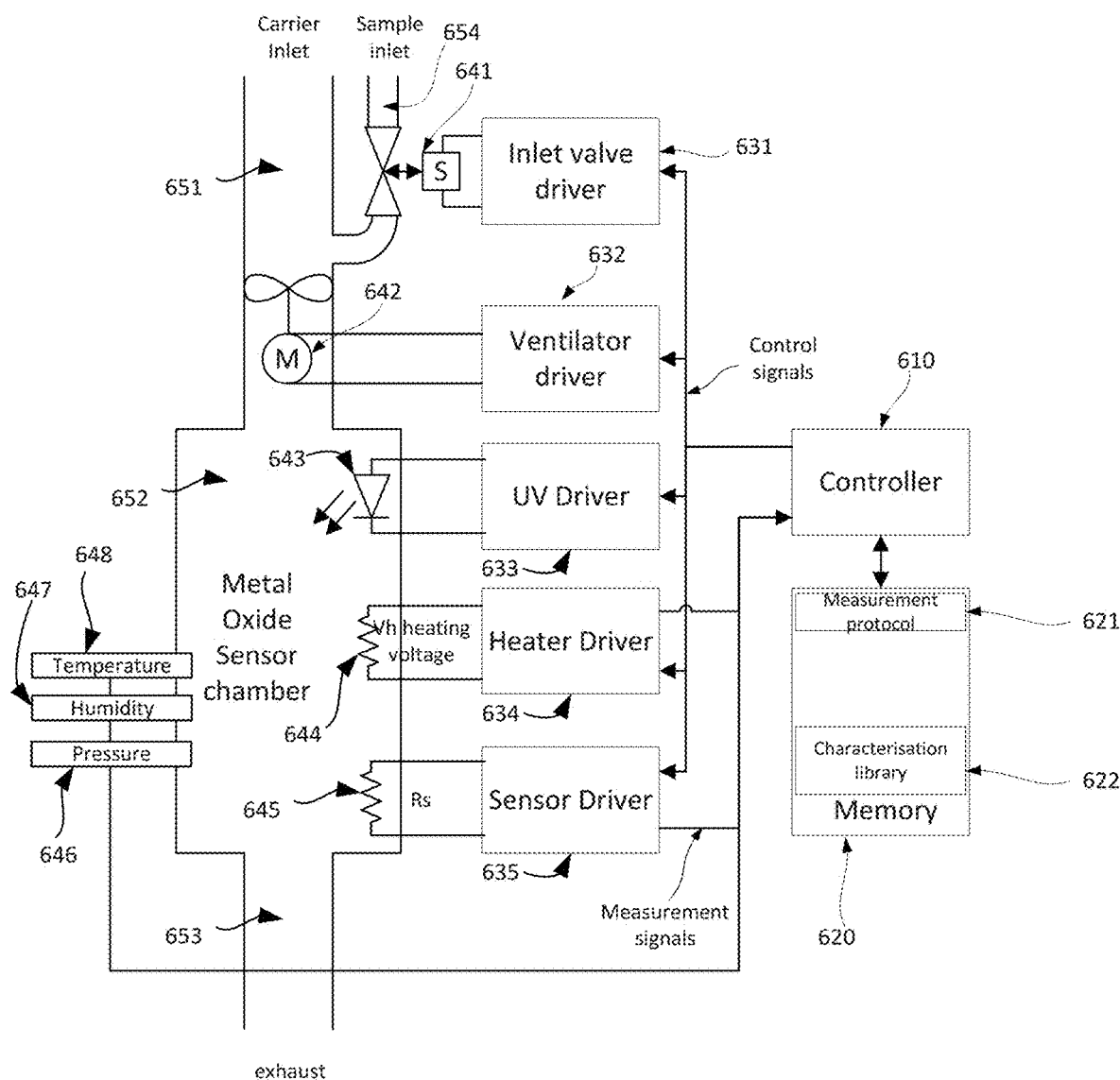
FIG. 6 shows a first embodiment.

FIG. 6 shows a first embodiment. As shown in FIG. 6 there is provided a machine olfaction system. The machine olfaction system comprises a controller 610, which is in communication with an inlet valve driver 631, ventilator driver 632, UV driver 633 heater driver 644 and a gas sensor driver 645, and a memory 620. The inlet valve driver 631 is coupled to an inlet valve actuator 641, ventilator driver 632 is coupled to a ventilator motor 642, UV driver 633 coupled to an Ultra Violet light source 643, which may comprise one or more LEDs, heater driver 644 and gas sensor driver 645 coupled to the heater and sensor terminals of a gas sensor. It will be appreciated that the system may incorporate different or additional drivers corresponding to different or additional experimental factors which might be modulated in accordance with embodiments of the invention. For example, the system may incorporate one or more chemical filters, which may be modulated by controlling the temperature of the filter.

As shown, the UV light source 643 and gas sensor comprising heating loop 644 and sensor loop 645 are situated in a gas sensor chamber 652. This chamber receives an incoming gas flow from a carrier inlet 651 and exhausts gas through exhaust 653. The inlet 651 may be supplied with a neutral carrier gas, or may simply use ambient air, or any other fluid depending on the specifics of the implementation. In some embodiments the exhaust may loop back to the inlet. As shown the gas to be characterised is injected into the gas flow arriving through the inlet 651 via a sample inlet 654.

In this context, the term gas should be understood in the broadest possible sense, as discussed above or otherwise. In particular, a gas includes any sample in a substantially gaseous phase. This may include particles of solid or liquid dispersed in a gaseous carrier. This may include a gas comprising only one, or a plurality of different molecules, some or all of which may correspond to the sample to be characterised, while others may be inert or otherwise merely serve as carriers, and not to be characterised.

It should also be born in mind that the phase of matter of the sample is of significance in that it is in this phase that the sample is expected to react with the gas sensor. It is entirely possible that in parts of the system away from the gas sensor, the sample may exist in another form. In particular, the sample may circulate in a liquid, and be separated from that liquid to take a gaseous form at the relevant point by means of a semi-permeable membrane etc.

In some cases, for example where the gas to be characterised is the ambient air, the mixing of carrier and sample gases in this way may not be necessary. The ventilator 642 acts to draw the carrier and sample gases through the inlet 651 and to impel it through the gas sensor chamber 652 and out of the exhaust 653 in a controlled manner, ensuring a desired flow rate and pressure. In some implementations, for example those operating on a permanent basis, it may be desirable to ensure an airflow through the gas sensor chamber whenever the gas sensor is under power, to avoid overheating or damage from long term use. A ventilator may be situated on the exhaust side of the gas sensor chamber as well as or instead of the ventilator 642 of this embodiment. In the arrangement shown, the flow of air caused by the action of the ventilator 642 will act to draw the gas to be characterised through the sample inlet by means of a venturi effect, however in alternative implementations it may be desirable to provide separate propulsion means for the gas to be characterised.

In operation, the controller retrieves a measurement protocol 621 from the memory 620, and sets the parameters of each of the drivers in accordance with the measurement protocol. These parameters are stepped through a number of different values successively, and the outputs of the sensor monitored. Once the sequence defined in the measurement protocol is complete, the set of results obtained from the sensor are compared by the controller with the representative values stored in the characterization library, which is also stored in the memory. Optionally, if no satisfactory match is obtained, an alternative measurement protocol may be run and the process repeated. Once a match is identified in the characterization library, the corresponding characteristic is reported to the user via the display of the host device. At regular intervals, or as required, the controller may access a protocol server using a communications interface of the host device, to obtain additional or updated measurement protocols, and/or a new or updated characterization library.

Preferably, the selected measurement protocol will correspond as closely as possible to the type of sample to be characterised. The measurement protocol may be selected on the basis of any available information about the type of sample being characterised this may involve user input in order to provide any available information about the sample—for example, the user might specify that the sample was a particular foodstuff type, which may then provide a basis for preferentially selecting certain characterisation libraries. Alternatively, the system may communicate with other devices to obtain relevant information—for example, a connected refrigerator may be able to provide information about its contents, or product packaging may have bar codes, RFID tags or other identifiers that can be used to retrieve additional information supporting optimal selection of the characterisation library.

Accordingly, there is provided a system for characterizing a gas, comprising a gas sensor and a controller, wherein the controller is adapted to modify two or more operating conditions of the gas sensor during a measurement cycle, where a measurement cycle starts with an initial reading from the gas sensor and ends with a final reading from said gas sensor, and comprises a plurality of measurements sufficient for the characterization. More particularly, there is provided a system for characterizing a gas, comprising a gas sensor, a controller and a plurality drivers, each driver controlling a transducer operable to determine a respective operating condition of the gas sensor, wherein the controller is in communication with the drivers so as to modify a respective plurality of operating conditions of the gas sensor during a measurement cycle, where a measurement cycle starts with an initial reading from the gas sensor and ends with a final reading from said gas sensor, and comprises a plurality of measurements sufficient for the characterization.

Figure 7:
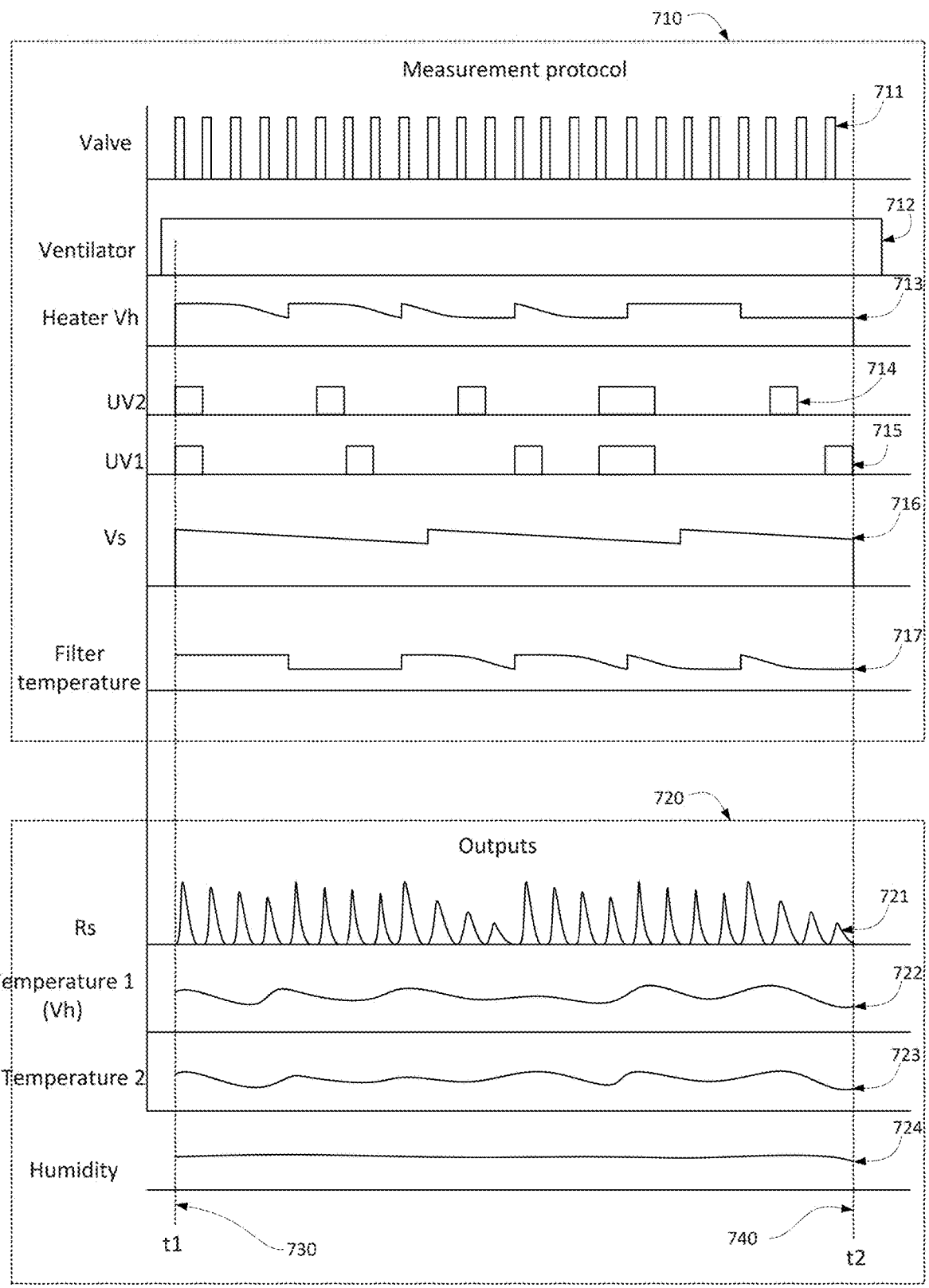
FIG. 7 illustrates a measurement protocol and resulting measurements.

FIG. 7 illustrates a measurement protocol and resulting measurements.

As shown in FIG. 7, a measurement protocol 710 can be represented as a set of waveforms corresponding to the different settings of the inlet valve driver 631, ventilator driver 632, UV driver 633 heater driver 644 and gas sensor driver 645. Specifically as shown a first waveform 711 represents the desired setting for the inlet valve driver 631 throughout the measurement cycle, a second waveform 712 represents the desired setting for the ventilator driver 632 throughout the measurement cycle, a third waveform 713 represents the desired setting for the heater driver 644 throughout the measurement cycle, a fourth waveform 714 represents a first desired setting for the UV driver 633 throughout the measurement cycle, a fifth waveform 715 represents a second desired setting for the UV driver 633 throughout the measurement cycle, and a sixth waveform 716 represents the desired setting Vs for the gas sensor driver 645 throughout the measurement cycle. Vs means a voltage to be provided to sensing material of the sensor.

Additionally, the sensor can be operated by current source instead of voltage source A seventh waveform 717 represents the desired setting for the chemical filter temperature driver. The number of wave forms will of course vary depending on the number of factors selected for variation throughout the measurement cycle, and may exclude some of the values described in this embodiment, and may equally incorporate additional or alternative factors.

Any combination of two or more operational parameters, such as those described above, or otherwise, may be varied during the measurement cycle. The parameters selected to be varied will generally be those best suited to the type of sample to be characterised. For example, for certain sample categories, a measurement program setting various combinations of UV irradiation frequency and temperature may be found to be particularly effective in differentiating between different samples, whilst in other sample categories, a measurement program setting various combinations of UV irradiation frequency and UV pulse frequency may be found to be particularly effective, and so on. Similarly, depending on the context it may be desirable to vary more than two operational parameters, as shown in FIG. 6.

As shown, the Valve 654 controlled by the inlet valve driver 631 is opened periodically to permit the gas to be characterised enter the airstream through the sensor chamber 652, during which time, the output of the gas sensor 645 can be observed to rise to a peak as it reacts to the gas to be characterised to a greater or lesser extent depending on the composition of the gas, the characteristics of the sensor, and the other operating parameters set in accordance with the measurement protocol. As shown, at a predetermined interval after the valve 654 is opened, it is shut again, cutting of the egress of the gas to be characterised, during which time, the output of the gas sensor 645 can be observed to fall back from its peak value to a baseline as the gas to be characterised diffuses away from the gas sensor's reactive surface at a rate depending on the composition of the gas, the characteristics of the sensor, and the other operating parameters set in accordance with the measurement protocol.

The system further comprises a pressure sensor 646, humidity sensor 647 and temperature sensor 648.

As shown, the ventilator 712 is driven by a constant wave form, providing a constant flow of air through the gas sensor chamber. In other embodiments the flow rate may be modulated in as one of the operating parameters varied during the measurement cycle to better characterise the sample gas. As shown, the ventilator starts some time before t1, and stops sometime after t2, to provide cooling for the gas sensor and to ensure that the air in the chamber is clean at the start and end of the cycle.

Figure 1:
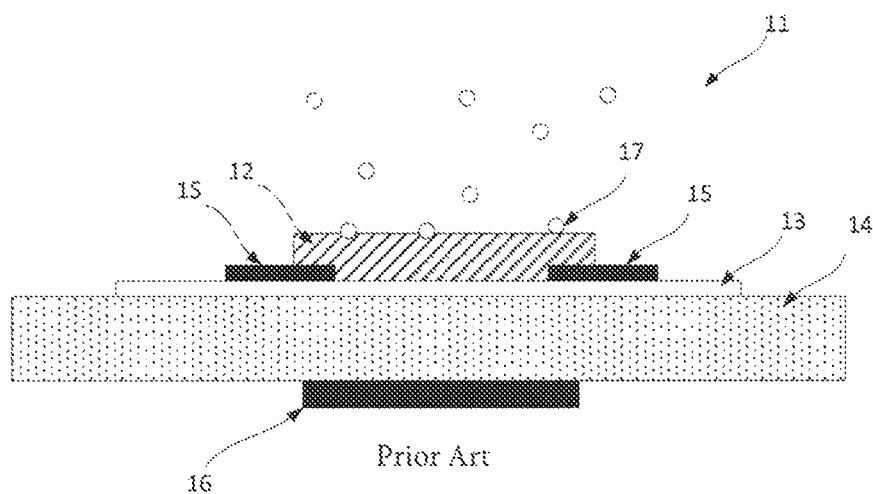
FIG. 1 is a cross-sectional view which illustrates, schematically, the basic structure of a first prior art semi-conducting metal-oxide type gas sensor.
Figure 2:
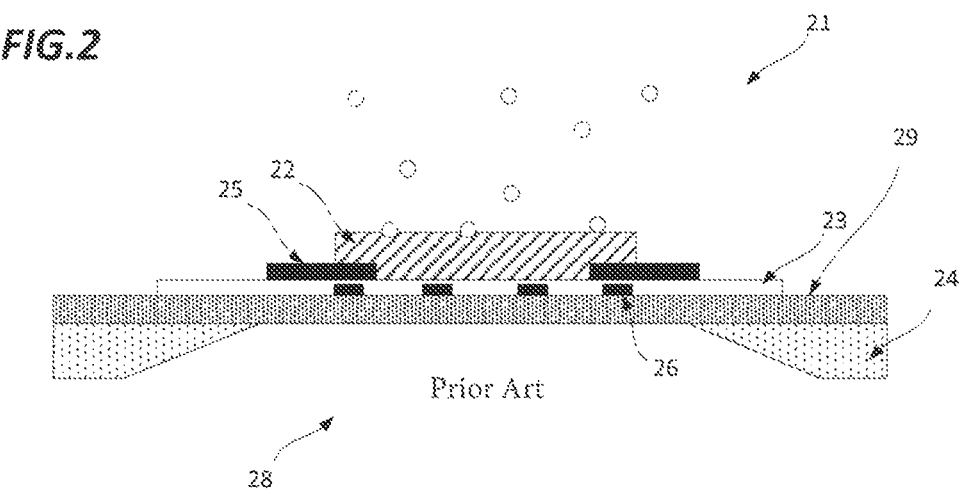
FIG. 2 is a cross-sectional view which illustrates, schematically, the general structure of a prior art semi-conducting metal-oxide type gas sensor having a micro-hotplate structure.
Figure 3:
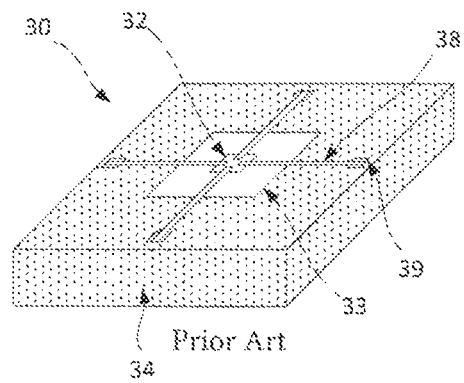
FIG. 3 illustrates a prior art sensor having a first type of micro-hotplate architecture.
Figure 4:
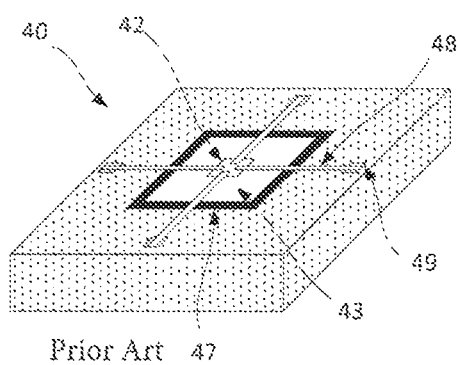
FIG. 4 illustrates a prior art sensors having a second type of micro-hotplate, with a suspended architecture.

As described with regard to FIGS. 2, 3 and 4, a gas sensor device conventionally incorporates a heater loop. This heater generally comprises a resistive component which emits heat in a predictable manner when a specified voltage is applied. In accordance with embodiments of the present invention, the voltage applied to the heater Vh is varied throughout the measurement cycle as one of the operating parameters varied during the measurement cycle to better characterise the sample gas.

Two separate waveforms 714, 715 are shown form the UV driver, on the basis that the UV source 643 may comprise an array of (in this case two) UV LEDs, selected to emit different Ultra-Violet wavelengths. In accordance with this embodiment, these two UV LEDs are controlled independently, and as such may be both on, both off, or one may be on and the other off. While the waveform shown is limited to turning the LEDs on or off, it will be appreciated that it may also be desirable to modulate the intensity of the LEDs during the measurement cycle. While this embodiment is described in terms of standard LEDs with substantially fixed characteristic wavelengths, other technologies may make it possible to specify the desired wavelength of a light source, in which case additional data may be incorporated in the measurement protocol to specify the desired wavelength a different points of the measurement period.

The UV modulation may operate in a pulse mode, whereby a UV pulse train having a specified frequency is switched between pulse train frequencies, offering an increase in sensitivity and selectivity.

Ultraviolet (UV) light can be used to enhance sensitivity and selectivity of metal oxide sensors.

In aspect of the similar phenomena, a pulsed UV illumination is much more efficient to increase sensitivity in comparison with constant UV illumination. Additionally, an ultraviolet lamp consumes a lot of power, and it is not therefore optimal for some mobile terminal implementations where power is a major consideration. A UV LED is generally a more efficient way to make high frequency pulsed UV lighting.

The waveform 716 is used to drive the gas sensor itself. In conventional systems this is a passive component whose resistance varies in response to its reaction to certain components of the gas to be characterised. In accordance with certain embodiments of the present invention however, by varying the voltage across the device its interaction with certain components of the gas to be characterised can be modified, for example on the basis of chemical potential of adsorbed particles at the surface. Thus in certain embodiments this voltage is varied throughout the measurement cycle as one of the operating parameters varied during the measurement cycle to better characterise the sample gas. The waveform 716 represents such a variation.

This waveform may also exhibit a pulse function providing electric pulse to the sensing material which can be effective to increase sensitivity and to reduce recovery time for the metal oxide sensor in comparison with an ordinary driving circuit for a specific gas. Various driving waveforms are appropriate, in particular those known for use in electrical systems for analysis by means of a transfer function.

The waveform 717 is used to drive a chemical filter, which may be disposed on or near the gas sensor. In accordance with certain embodiments of the present invention, by varying the temperature of the filter its interaction with certain components of the gas to be characterised can be modified, and thereby control the concentrations of certain gases reaching the sensor 645. Thus in certain embodiments this voltage is varied throughout the measurement cycle as one of the operating parameters varied during the measurement cycle to better characterise the sample gas. The waveform 717 represents such a variation.

Each of the waveforms 711, 712, 713, 714, 715, 716, 717 is represented as a continuous waveform, however in practice the measurement protocol will be defined by a set of digital values representing instantaneous settings for the respective drivers throughout the measurement period. These digital values may indicate the desired setting at regular intervals throughout the measurement period, or each setting value may have an associated time value, so that settings can be specified for any arbitrary instant during the measurement period as desired.

While as shown the waveforms start at a time t1 730 and end at a time t2 740, which correspond to the initial reading from said gas sensor and the last reading from said gas sensor respectively, in some embodiments certain waveforms may extend into the period before t1, or after t2. In particular, it may be desirable to modulate any of the factors under control in a particular manner to ensure that the gas sensor is fully cleaned before measurements start, or once they are complete.

As described above, the operating conditions of the gas sensor are varied during a measurement cycle, and a plurality of measurements sufficient to characterise the sample gas is taken throughout this cycle.

FIG. 7 shows exemplary measurement values. In particular as show, the sample is characterised by measurements of the resistance of the gas sensor 721.

The sample is additionally characterised by a first temperature measurement 722 from the heater of the gas sensor

644. Although the primary role of the heater 644 is to heat the gas sensor, it is possible to deduce device temperature on the basis of changes in the device's resistance as compared to a theoretical resistance radiating freely.

The sample is further characterised by a second temperature measurement 723 from temperature sensor 648, and a humidity measurement 724 from humidity sensor 647.

These readings 722, 723, 724 may not directly characterise the sample gas, however these ambient conditions can significantly affect the behaviour of the gas sensor, and as such may be used in the selection of or comparison with the characterisation library 622 as discussed hereafter or can be used for calibration and compensation in comparison with the characterisation library.

Each of the waveforms 721, 722, 723, 724 is represented as a continuous waveform, however in practice the measurements will often take the form of sequences of digital values representing instantaneous samples from the respective drivers and sensors. These samples may be taken at regular intervals during the measurement cycle. These samples may also be taken at predetermined times during the measurement cycles. In this case, the measurement protocol may additionally contain data specifying the times during the measurement cycle at which readings should be taken in parallel with the values to be set for each of the operating conditions.

In addition to sampling the outputs of the various drivers and sensors, the system may process the sampled information to further characterise the readings, for example by extracting peak values, time to rise to a particular value, or to a peak value, time to rise to a specified proportion of a peak value, time to fall to zero from a peak value, time to fall to fall to a specified proportion of a peak value, time to fall to fall to a specified value, time to fall to zero, peak rise rate, rise rate at a specified point in the measurement cycle, peak fall rate, fall rate as a specified point in the measurement cycle, etc. The system may calculate mean values, standard deviations or other statistical evaluations. The system may perform curve fitting or regression analysis, noise reduction, and baseline adjustment. Instructions specifying which such calculations are to be performed on the basis of which measurements may be incorporated in the measurement protocol.

As such, the final sample characterisation may comprise raw reading data, processed representations of the sample data or a combination of both. The measurement protocol may specify any processing to be performed. The measurement protocol may specify which raw readings are to be the subjects of processing. The measurement protocol may specify the format and structure of the final sample characterisation.

Once the final sample characterisation is complete, the controller 610 will select a characterisation library 622 from the memory 620. The characterisation library may be selected on the basis of any available information about the type of sample being characterised, and the ambient conditions in place at the time of the measurement cycle. This may involve user input in order to provide any available information about the sample—for example, the user might specify that the sample was a particular foodstuff type, which may then provide a basis for preferentially selecting certain characterisation libraries. Alternatively, the system may communicate with other devices to obtain relevant information—for example, a connected refrigerator may be able to provide information about its contents, or product packaging may have bar codes, RFID tags or other identifiers that can be used to retrieve additional information concerning the sample. Different libraries may in some cases be applicable depending on the readings of ambient conditions such as temperature, pressure and humidity. The selection of library may be determined on the basis of, or influenced by, the measurement protocol in use.

Each characterisation library comprises a plurality of characterisation targets. A characterisation target is a representative set of data corresponding to the data in the sample characterisation, together with classification data. Characterisation targets may be provided representative of different sub-categories of the type of sample under study. For example if the sample type is "Coffees", a characterisation target may be provided for each combination of multidimensional characteristics that may classify a particular sample (species, origin, condition, taste profile, quality, etc.), or alternatively, separate characterisation may be provided for each dimension, which may be applied separately to the sample characterisation, and combined to provide the final complete classification of the sample.

Figure 8A:
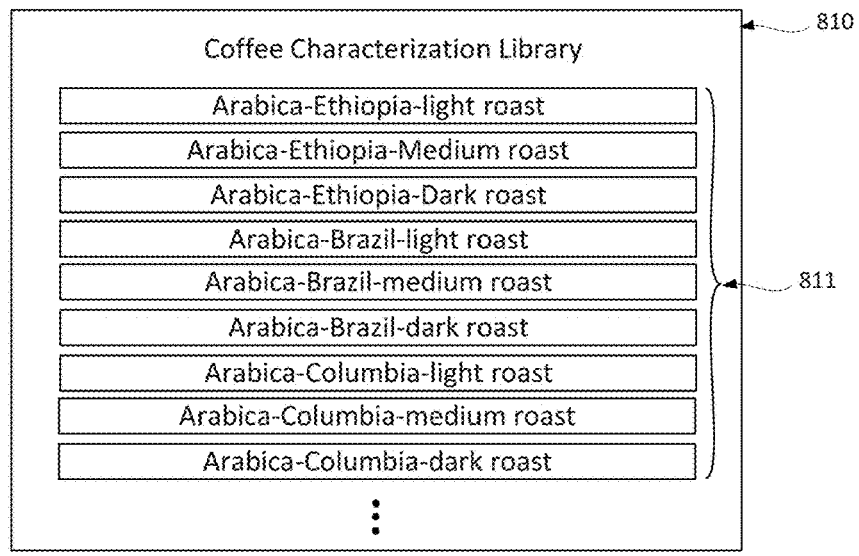
FIG. 8a shows a first characterisation library architecture.
Figure 8B:
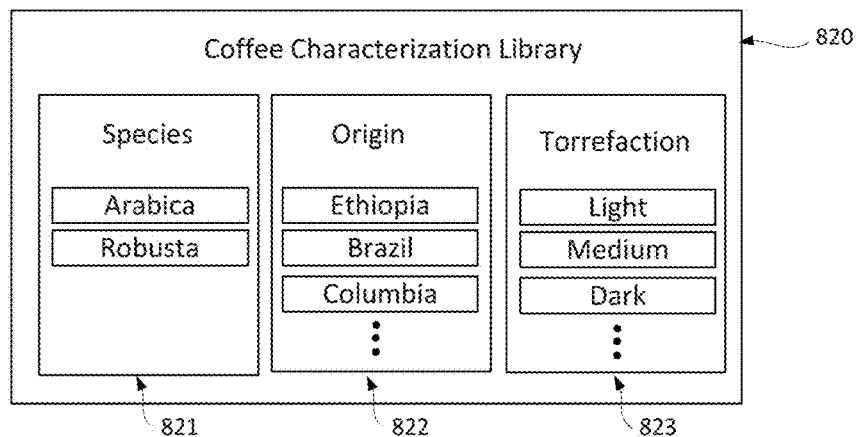
FIG. 8b shows a second characterisation library architecture.
Figure 8C:
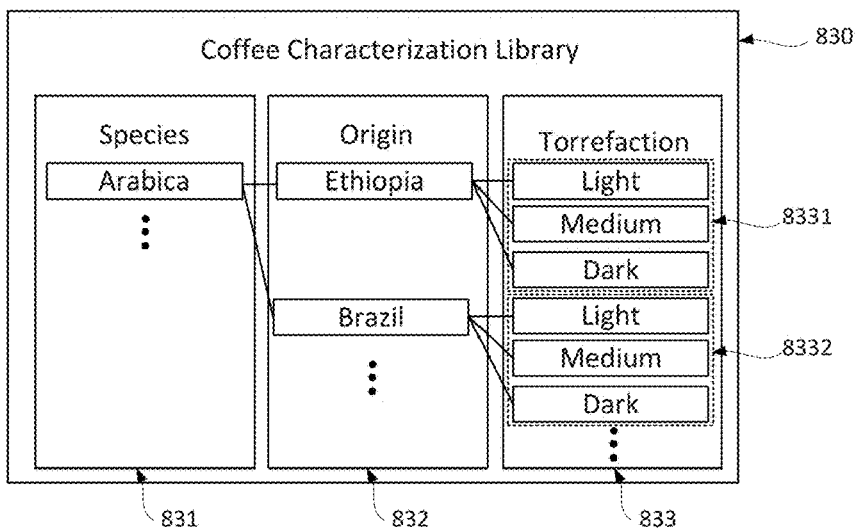
FIG. 8c shows a third characterisation library architecture.

FIGS. 8a, 8b and 8c show alternative structures for the characterisation library. As discussed above, in accordance with certain embodiments, a sample characterisation is compared with a characterisation library containing a plurality of characterisation targets. A characterisation target contains a set of data representative of a particular classification which might be applied to sample. These target characterisations are compared with the sample characterisation, and when a match is identified, the sample is associated with the corresponding classification.

The comparison process may be carried out by means of multivariate analysis techniques such as k-NN (k-Nearest Neighbour), CA (Cluster Analysis), DFA (Discriminant Function Analysis), PCA (Principal Component Analysis), PCR (Principal Component Regression) Multiple Linear Regression (MLR), hierarchical cluster analysis (HCA), ANN (Artificial Neural Networks), Fuzzy-ART, PNN (Probabilistic Neural Network), LVQ (Learning Vector Quantization), SOM (Self Organizing Map) and so on. The analysis may also make use of neural network and fuzzy logic technologies, such as Back Propagation, Multilayer perceptron, Radial Basis Function, Adaptive Resonance Theory, and the like.

In the example of FIGS. 8a, 8b and 8c, there are shown three alternative architectures of characterisation libraries for the characterisation of coffee.

FIG. 8a shows a first characterisation library architecture. As shown in FIG. 8a, the library 810 comprises a set of characterisation targets 811. Each characterisation target 811 corresponds to a specific combination of characteristics. In operation, the sample characterisation is compared to each of these characterisation targets, and the classifications associated with whichever target gives the best match are applied to the sample. This is the simplest of the three approaches described with respect to FIG. 8, and is most suited to cases where there are relatively few dimensions to the classifications (in this case we have three dimensions—species, origin and roasting), and/or relatively few options for each dimension.

FIG. 8b shows a second characterisation library architecture. As shown in FIG. 8b, the library 820 comprises a set of characterisation sub-libraries 821, 822, 823. Each of these sub libraries corresponds to one of the three dimensions of the classification to be applied to the sample. Specifically, sub-library 821 contains classification targets relating to the species of the coffee, sub-library 822 contains classification targets relating to the origin of the coffee, and sub-library 823 contains classification targets relating to the roasting of the coffee. In operation, the sample characterisation is compared to each of the characterisation targets in each sub library, and the classification associated with whichever target gives the best match from each sub-library are applied to the sample. This approach is better suited to implementations handling a larger number of dimensions of classification, or where each dimension has a large number of associated classifications.

FIG. 8c shows a third characterisation library architecture. As shown in FIG. 8c, the library 830 comprises a set of characterisation sub-libraries 831, 832, 833. Each of these sub libraries corresponds to one of the three dimensions of the classification to be applied to the sample. Specifically, sub-library 821 contains classification targets relating to the species of the coffee, sub-library 822 contains classification targets relating to the origin of the coffee, and sub-library 823 contains classification targets relating to the roasting of the coffee. Furthermore, there is a hierarchical relationship between the sub-libraries, with each characterisation target in the first sub library 831 pointing to certain characterisation targets in the second library 832, and each characterisation target in the second sub library 832 pointing to certain characterisation targets in the third library 833. In operation, the sample characterisation is compared to each of the characterisation targets in the first sub library 831, and then compared to each of the characterisation targets in the second sub library 832 referenced by the best match identified in the first library, before finally being compared to each of the characterisation targets in the third sub library 833 referenced by the best match identified in the second library. By this means, the total number of comparisons performed may be less than are necessary in the embodiment of FIG. 8b, and the characterisation targets can be fine-tuned to correspond to samples belonging to the higher level characterisation targets with which they are associated. On the other hand, this approach may lead to larger classification libraries, since in some cases similar characterisation targets will be needed for each of the classification targets in the next level up, for example 8331 and 8332 as shown. This may lead to partial duplication of characterisation targets in the library. The classification associated with whichever target gives the best match from each sub-library are applied to the sample. This approach is better suited to implementations handling a larger number of dimensions of classification, or where each dimension has a large number of associated classifications, in terms of performance, albeit at the price of larger libraries in some cases.

Generally, the measurement protocol and the characterisation library are matched to the sample type. In many cases, improved performance can be expected by defining the measurement protocol to optimally discriminate between likely candidates of a given type, and to exclude likely sources of confusion in that context. Similarly, improved performance can be expected by defining the characterisation library to optimally discriminate between likely candidates of a given type on the basis of the data expected from the measurement protocol, and to exclude likely sources of confusion in that context. On this basis, the measurement protocol and the characterisation library may be created as a matching pair, designed from the ground up to ask the right questions, and interpret the answers in full cognisance of the subtleties of those questions, and the context in which they are asked.

The measurement protocol and characterisation library may be defined by means of a learning process, during which an automated procedure will allow screening specimen samples with known classifications under all stimuli and parameters with varying intensity and duration. Results may be based on a transfer function, taken as a black box, where the classifications of the specimen sample and intensity of exposure are taken as inputs. Outputs are collected into a database. Optimisation of a given application will also extract only the most relevant features specific to the application.

In one approach to defining the measurement protocol and the characterisation library, all combinations of different operating conditions corresponding to those that the final measurement system is able to modulate, for example as described with reference to FIGS. 6 and 7, are applied sequentially to a set of representative samples. Measurements for each of the variables that the final measurement system is able to detect at a predetermined sampling rate, for example, every second for a measurement cycle of 10 minutes.

The variables might be sensor responses but also characteristic derivative values due to the temperature modulation for example, such as Reaction Start Time (RST), Recovery Time, Delay time (the delay between the response of different sensors, where applicable), response inflection point, etc.

This process will provide matrix of x variables (response at fixed time intervals for example) versus y samples.

This matrix will often be large, but a variety of algorithms are known for the identification of critical variable and characteristic results enabling the quantification of a gas and discrimination of samples, for the range outlined by the set of representative samples. Such algorithms may include multivariate analysis techniques such as k-NN (k-Nearest Neighbour), CA (Cluster Analysis), DFA (Discriminant Function Analysis), PCA (Principal Component Analysis), PCR (Principal Component Regression) Multiple Linear Regression (MLR), hierarchical cluster analysis (HCA), ANN (Artificial Neural Networks), Fuzzy-ART, PNN (Probabilistic Neural Network), LVQ (Learning Vector Quantization), SOM (Self Organizing Map) and so on.

Based on the variables selected, the relevant operating conditions allowing the readings of these variables will be known. These algorithms are capable of identifying pertinent variables to solve the application. The algorithms are furthermore capable of detecting not only characteristic values and derivative characteristics, but also characteristic groupings, which may comprise characteristic output values and derived characteristics occurring together for a particular sample with a particular drive signal.

On this basis, it is thus possible to select the measurement protocol (i.e. the only relevant operating conditions to use), and define the characterization library which may comprise characteristic values, derived characteristics, characteristic groupings, associated operating conditions, etc, based on the matrix restricted to the known samples and the operating conditions selected for use in the measurement protocol.

Figure 9:
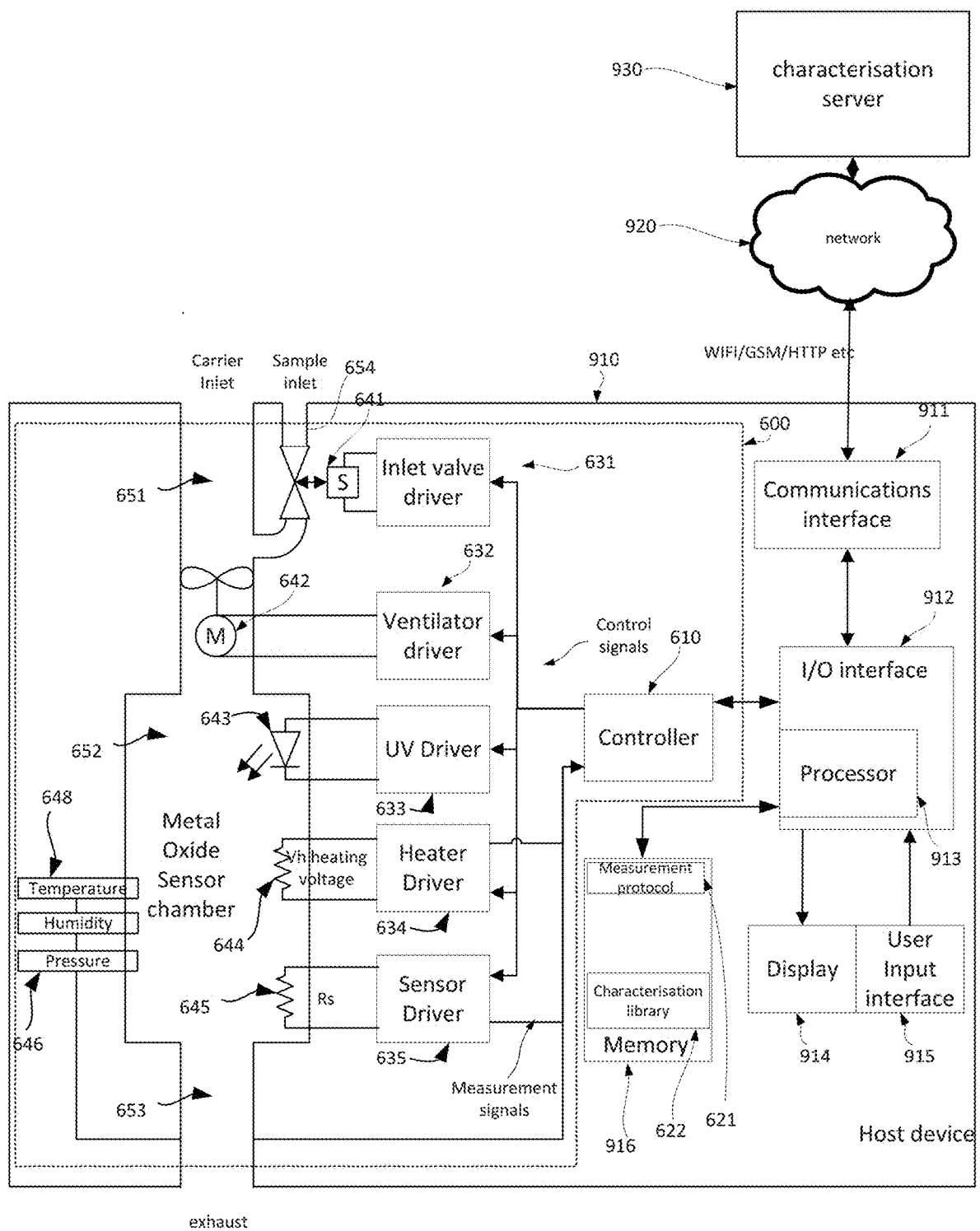
FIG. 9 shows an integration of the system of FIG. 6 into a user device.

FIG. 9 shows an integration of the system of FIG. 6 into a user device.

As shown in FIG. 9, a machine olfaction device 600 is integrated with a host device 910 such as a mobile telephone handset. The machine olfaction device is similar in structure and operation to that described with respect to the foregoing embodiments. Furthermore, as shown, the machine olfaction device 600 is in communication with a processor 912 of the host device 910 via the I/O interface 912 of the user device 910. The Processor 912 is additionally in communication with a communications interface 911, a display 914 and a user input interface 915.

The memory 916 of the user device may be used to store the measurement protocol 621 and the characterisation library 622, and the processor 913 may provide some of the functionality previously ascribed to the controller, for example in retrieving the measurement protocol from memory, issuing instructions to the drivers 631, 632, 633, 634, 635 via the controller 610, receiving an compiling the sample characterisation, performing any additional processing, comparing the final sample characterisation with the characterisation library, and reporting the results to the user via display 914. At various stages of the operation further inputs, for example concerning the sample type, may be prompted via the display 914, and recovered via the user input interface 915.

Additionally, the processor may communicate via a communications interface with external resources. For example, the communications interface may support communications protocols such as Ethernet, WIFI, Bluetooth, or cellular telephone network communications, possibly enabling communications a network 920 by means of which the processor may communicate with an external server 930. This server may offer an extended repository of measurement protocols and characterisation libraries. By this means, where a user wishes to perform a characterisation for which no suitable measurement protocol and characterisation library is available in the memory 916, the processor 913 may interrogate the characterisation server 930, and download a suitable measurement protocol and characterisation library. The characterisation server may also make available updated measurement protocols and characterisation libraries, as new classifications are developed (for example corresponding to new product categories) or with additional refinements to measurement protocols or characterisation libraries permitting improved performance. Still further, the processor may communicate with the characterisation server concerning the sample characterisations it receives, and the results of the categorisations it performs. This information may be assessed at the characterisation server to identify weaknesses in measurement protocols and characterisation libraries, the emergence of new sample types, and the like. Such information may indeed be fed directly into the measurement protocol and characterisation library definition process, so that new measurement protocols and characterisation libraries are built on the results of previous implementations.

Alternatively, the characterisation server may provide some of the functionality previously ascribed to the controller, for example in retrieving the measurement protocol from memory local to the server, issuing instructions to the drivers 631, 632, 633, 634, 635 via the network 920, processor 912 and controller 610, receiving an compiling the sample characterisation, performing any additional processing, comparing the final sample characterisation with the characterisation library, or transmitting the results back to the user device for display 914. It will be appreciated the characterisation server may provide some of these functions, whilst leaving others to be implemented locally. For example, the measurement protocol may be stored locally to the device, and implemented by the device's controller, but receiving and compiling the sample characterisation, performing any additional processing, comparing the final sample characterisation with the characterisation library, and transmitting the results back to the user device for display 914 may be performed on the server side, or vice versa.

Figure 10:
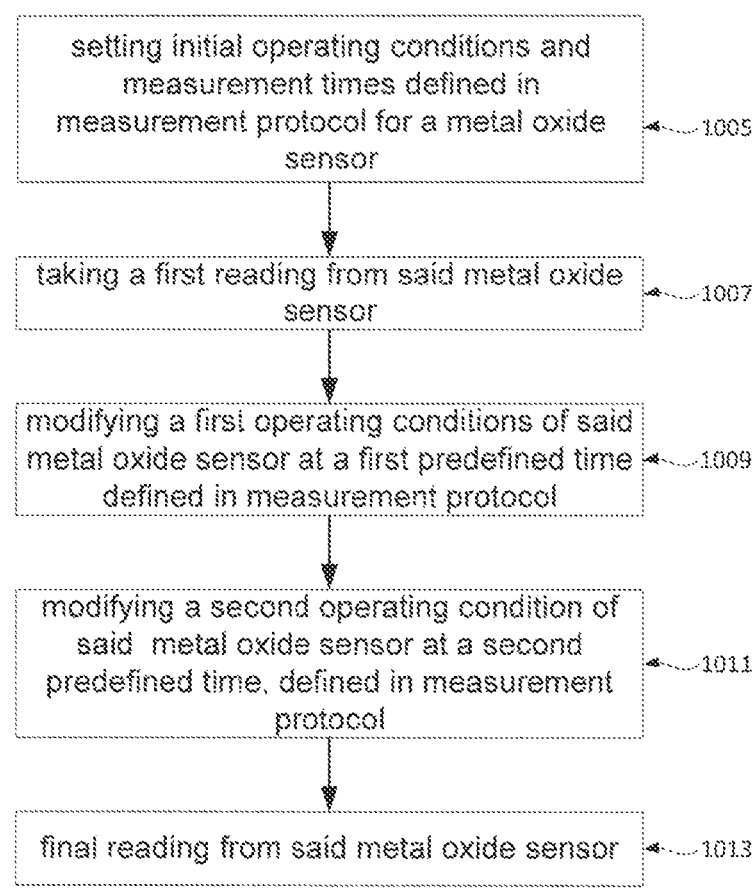
FIG. 10 shows the steps of a method of characterizing a gas according to an embodiment.

FIG. 10 shows the steps of a method of characterizing a gas according to an embodiment. As shown, the method starts at step 1005 at which initial operating conditions for a gas sensor are set in accordance with a measurement protocol. The method next proceeds to step 1007 where a measurement cycle is initiated by taking a first reading from the gas sensor. The method then proceeds to step 1009 at which a first operating condition of the gas sensor is modified at a first predefined time in accordance with the measurement protocol. The method then proceeds to step 1011 at which a second operating condition of the gas sensor is modified at a second predefined time in accordance with the measurement protocol. In some embodiments, some or all of these steps may be iterated until a satisfactory result is achieved. The method then terminates the measurement cycle with a final reading from said gas sensor at step 1013.

Figure 11:
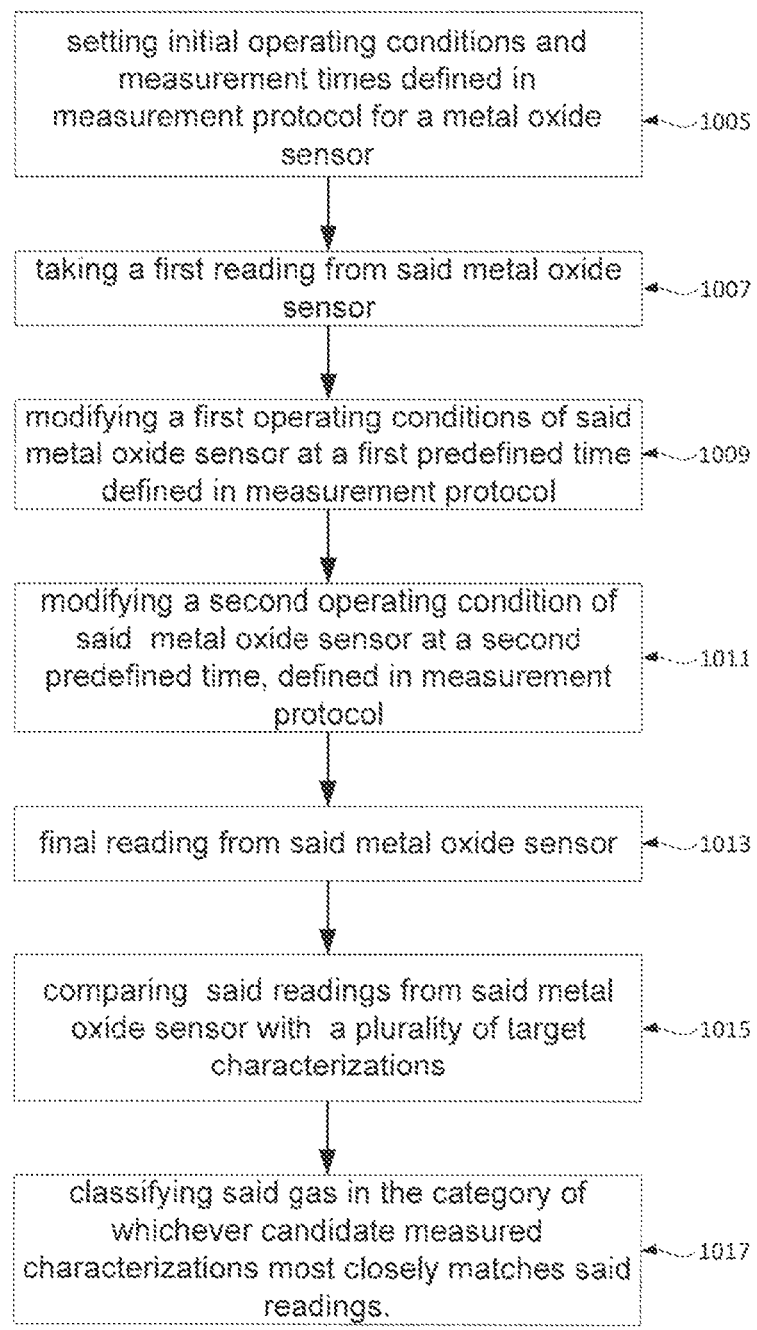
FIG. 11 shows the steps of a method of characterizing a gas according to a development of the embodiment of FIG. 10.

FIG. 11 shows the steps of a method of characterizing a gas according to a development of the embodiment of FIG. 10. Steps 1005 to 1013 correspond to those of the method of FIG. 10. As shown in FIG. 11, step 1013 is followed by step 1015 at which the readings from the gas sensor are compared with a plurality of target characterizations, each target characterization being associated with a respective category, before proceeding to step 1017 at which the gas is classified in the category of whichever target characterizations most closely matches said readings.

Figure 12:
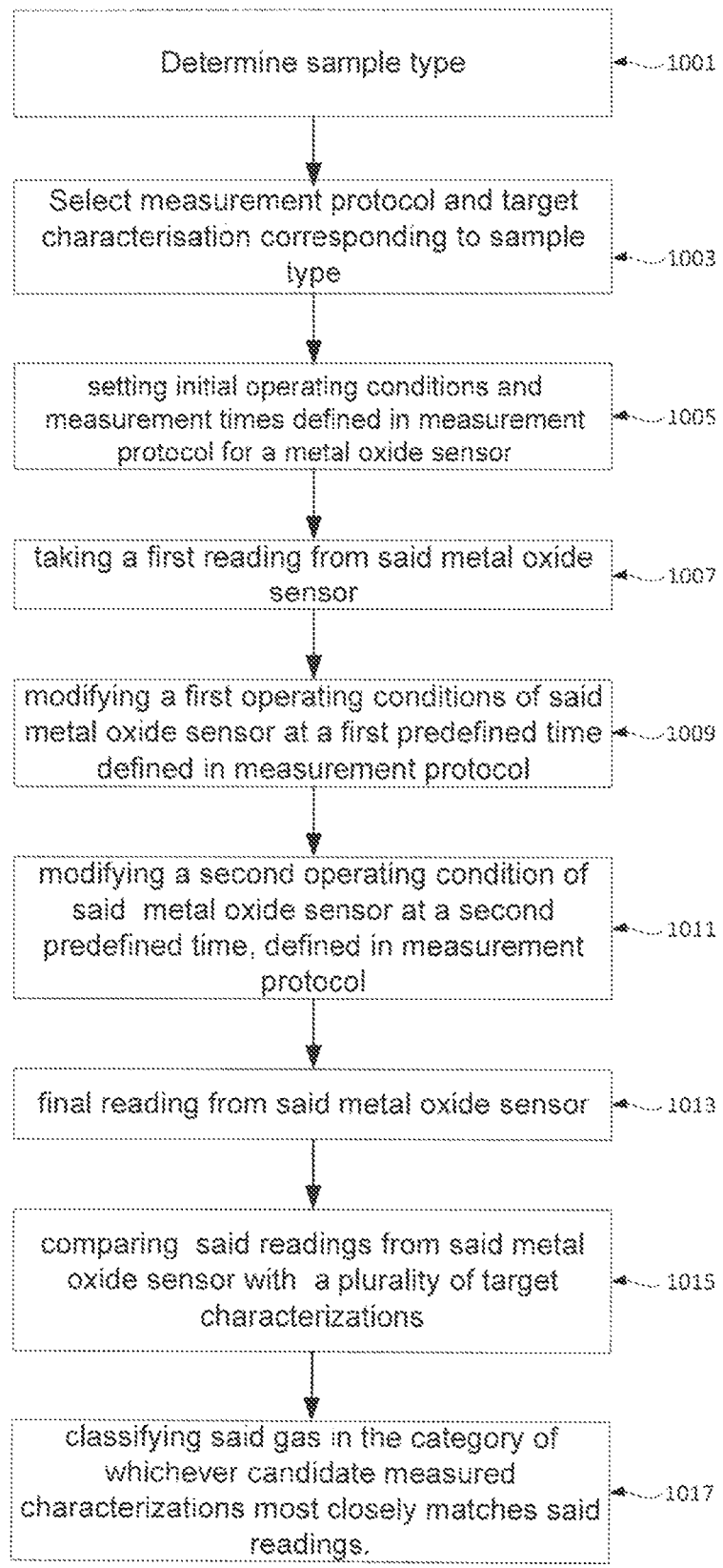
FIG. 12 shows the steps of a method of characterizing a gas according to a development of the embodiment of FIG. 11.

FIG. 12 shows the steps of a method of characterizing a gas according to a development of the embodiment of FIG. 11. Steps 1005 to 1017 correspond to those of the method of FIG. 11. As shown in FIG. 12, the method start with a step 1001 at which the sample type is determined, before proceeding to step 1003 at which a measurement protocol and plurality of target characterisations corresponding to the determined sample type are selected. The method then proceeds to step 1005 as described above, using the selected measurement protocol and target characterisations in the steps that follow.

In certain embodiments the determination of the sample type may be predetermined to some extend by the implementation itself, for example a system installed in a refrigerator will generally expect to deal with the classification of food products. The determination may also receive input from a user, who in the case of the examples of FIG. 8 for example may have preselected a "Coffee" sample type. Alternatively, the system may communicate with other devices to obtain relevant information—for example, a connected refrigerator may be able to provide information about its contents, or product packaging may have bar codes, RFID tags or other identifiers that can be used to retrieve additional information supporting optimal selection of the characterisation library. Still further the system may itself attempt to identify the sample type using its own olfactory capacity. In one such approach, if it seems that the available data is insufficient to make a definitive selection the system may attempt classification using a number of characterisation libraries, and choose from the results whichever represents the best match. This may incorporate not only the relative strength of the match, but also weightings from whatever context information is available. In another approach, the system may start with a more general characterisation library, and on the basis of this initial characterised select a more specific characterisation library, and so on until a final sample type is determined.

The methods described may incorporate the additional steps of transmitting the readings to a remote processor for comparison with a plurality of candidate measured characterizations, and receiving the characterization from said remote processor, for example as described above.

The methods described may incorporate the additional steps of generating the measurement protocol by determining at what times during a measurement cycle readings should be taken, and what values should be set for said first operating condition and said second operating condition to discriminate most clearly between said target characterizations, for example as described above.

Similarly, according to an embodiment, there is provided a method of generating the measurement protocol for use in the forgoing methods and devices, by determining at what times during a measurement cycle readings should be taken, and what values should be set for said first operating condition and said second operating condition to discriminate most clearly between said target characterizations, for example as described above.

The methods described may incorporate the additional steps of defining a set of target characterisations in a characterisation library corresponding to a particular sample type, by determining for a plurality of possible classifications of the sample of that type which sample characterisations arising from a specified measurement protocol would support the most discriminating matching between that classification and the sample characterisation.

Similarly, according to an embodiment, there is provided a method of defining a set of target characterisations in a characterisation library corresponding to a particular sample type, by determining for a plurality of possible classifications of the sample of that type which sample characterisations arising from a specified measurement protocol would support the most discriminating matching between that classification and the sample characterisation.

According to certain embodiments, an olfactometer or "electronic nose" is able to vary a plurality of operating parameters during a test cycle in parallel, in accordance with a measurement protocol. This measurement protocol, and correspondingly the operating parameters to be varied, the values to be set for those parameters, and the timing of the variation in these values is tailored to most effectively distinguish between likely candidates in a particular testing scenario. A characterisation library is then used to match the results of the measurement protocol to the best target in the characterisation library. Test protocols and/or characterisation libraries may be downloaded from a remote server on demand, and certain activities may be carried out either locally or remotely.

The disclosed methods can take form of an entirely hardware embodiment (e.g. FPGA), an entirely software embodiment (for example to control a system according to the invention) or an embodiment containing both hardware and software elements. Software embodiments include but are not limited to firmware, resident software, microcode, etc. The invention can take the form of a computer program product accessible from a computer-usable or computer-readable medium providing program code for use by or in connection with a computer or an instruction execution system. A computer-usable or computer-readable can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium.

These methods and processes may be implemented by means of computer-application programs or services, an application-programming interface (API), a library, and/or other computer-program product, or any combination of such entities.

Figure 13:
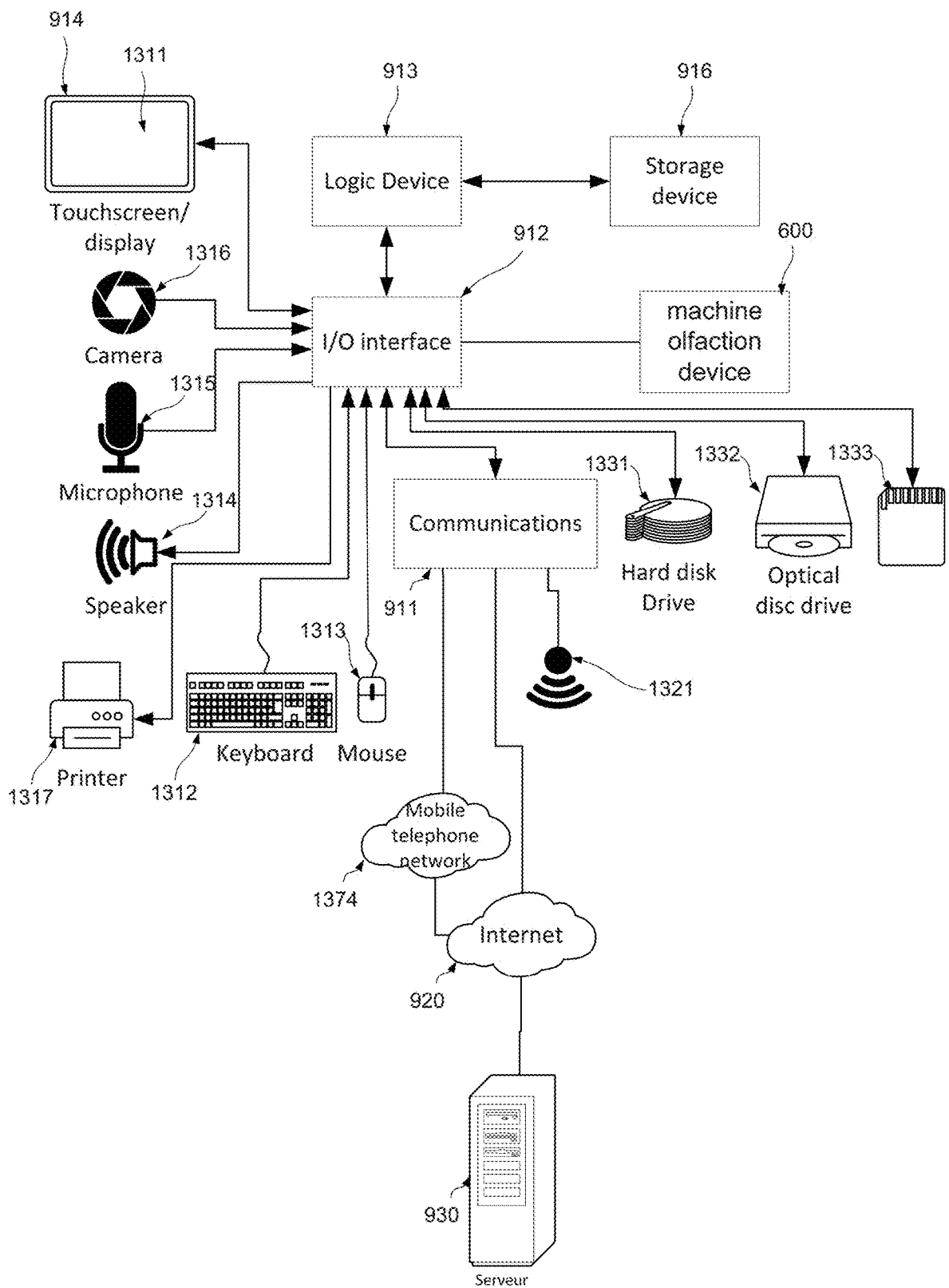
FIG. 13 shows a generic computing system suitable for implementation of embodiments of the invention.

FIG. 13 shows a generic computing system suitable for implementation of embodiments of the invention.

A shown in FIG. 13, a system includes a logic device 913 corresponding to the processor of FIG. 9 and a storage device 916 corresponding to the memory of FIG. 9. The system may optionally include a display subsystem 1311, input subsystem 1312, 1313, 1315, communication subsystem 911, and/or other components not shown.

Logic device 913 includes one or more physical devices configured to execute instructions. For example, the logic device 913 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic device 913 may include one or more processors configured to execute software instructions. Additionally or alternatively, the logic device may include one or more hardware or firmware logic devices configured to execute hardware or firmware instructions. Processors of the logic device may be single-core or multi-core, and the instructions executed thereon may be configured for sequential, parallel, and/or distributed processing. Individual components of the logic device 913 optionally may be distributed among two or more separate devices, which may be remotely located and/or configured for coordinated processing. Aspects of the logic device 913 may be virtualized and executed by remotely accessible, networked computing devices configured in a cloud-computing configuration.

Storage device 916 includes one or more physical devices configured to hold instructions executable by the logic device to implement the methods and processes described herein. When such methods and processes are implemented, the state of storage device 916 may be transformed—e.g., to hold different data.

Storage device 916 may include removable and/or built-in devices. Storage device 916 may comprise one or more types of storage device including optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage device may include volatile, non-volatile, dynamic, static, read/write, read-only, random-access, sequential-access, location-addressable, file-addressable, and/or content-addressable devices.

In certain arrangements, the system may comprise an interface 912 adapted to support communications between the Logic device 913 and further system components, in particular the machine olfaction device 600. For example, additional system components may comprise removable and/or built-in extended storage devices. Extended storage devices may comprise one or more types of storage device including optical memory 1332 (e.g., CD, DVD, HD-DVD, Blu-Ray Disc, etc.), semiconductor memory 1333 (e.g., RAM, EPROM, EEPROM, FLASH etc.), and/or magnetic memory 1331 (e.g., hard-disk drive, floppy-disk drive, tape drive, MRAM, etc.), among others. Such extended storage device may include volatile, non-volatile, dynamic, static, read/write, read-only, random-access, sequential-access, location-addressable, file-addressable, and/or content-addressable devices.

It will be appreciated that storage device includes one or more physical devices, and excludes propagating signals per se. However, aspects of the instructions described herein alternatively may be propagated by a communication medium (e.g., an electromagnetic signal, an optical signal, etc.), as opposed to being stored on a storage device.

Aspects of logic device 913 and storage device 916 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "program" may be used to describe an aspect of computing system implemented to perform a particular function. In some cases, a program may be instantiated via logic device executing machine-readable instructions held by storage device. It will be understood that different modules may be instantiated from the same application, service, code block, object, library, routine, API, function, etc. Likewise, the same program may be instantiated by different applications, services, code blocks, objects, routines, APIs, functions, etc. The term "program" may encompass individual or groups of executable files, data files, libraries, drivers, scripts, database records, etc.

In particular, the system of FIG. 13 may be used to implement embodiments of the invention.

For example a program implementing the steps described with respect to FIG. 10, 11 or 12 may be stored in storage device 916 and executed by logic device 913. The communications interface 912 may receive Measurement Protocols and Characterisation Libraries from the characterization server 930, and upload sample type information or sample characterization data as discussed above. The Logic device 1001 may receive and compile the sample characterization, perform any additional processing, compare the final sample characterization with the characterization library, and report the results to the user via display 914. At various stages of the operation further inputs, for example concerning the sample type, may be prompted via the display 914, and recovered via the user input interface devices 1313, 1312 as described bed above under the control of a suitable program, or may interface with internal or external dedicated systems adapted to perform some or all of these processes.

Accordingly the invention may be embodied in the form of a computer program.

It will be appreciated that a "service", as used herein, is an application program executable across multiple user sessions. A service may be available to one or more system components, programs, and/or other services. In some implementations, a service may run on one or more server-computing devices.

When included, display subsystem 914 may be used to present a visual representation of data held by storage device. This visual representation may take the form of a graphical user interface (GUI). As the herein described methods and processes change the data held by the storage device 916, and thus transform the state of the storage device 916, the state of display subsystem 914 may likewise be transformed to visually represent changes in the underlying data. Display subsystem 914 may include one or more display devices utilizing virtually any type of technology. Such display devices may be combined with logic device and/or storage device in a shared enclosure, or such display devices may be peripheral display devices.

When included, input subsystem may comprise or interface with one or more user-input devices such as a keyboard 1312, mouse 1311, touch screen 1311, or game controller (not shown). In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, colour, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 911 may be configured to communicatively couple computing system with one or more other computing devices. For example, communication module of may communicatively couple computing device to remote service hosted for example on a remote server 930 via a network of any size including for example a personal area network, local area network, wide area network, or the internet. Communication subsystem may include wired and/or wireless communication devices compatible with one or more different communication protocols. As non-limiting examples, the communication subsystem may be configured for communication via a wireless telephone network 1374, or a wired or wireless local- or wide-area network. In some embodiments, the communication subsystem may allow computing system to send and/or receive messages to and/or from other devices via a network such as the Internet 920. The communications subsystem may additionally support short range inductive communications 1321 with passive devices (NFC, RFID etc).

Figure 14:
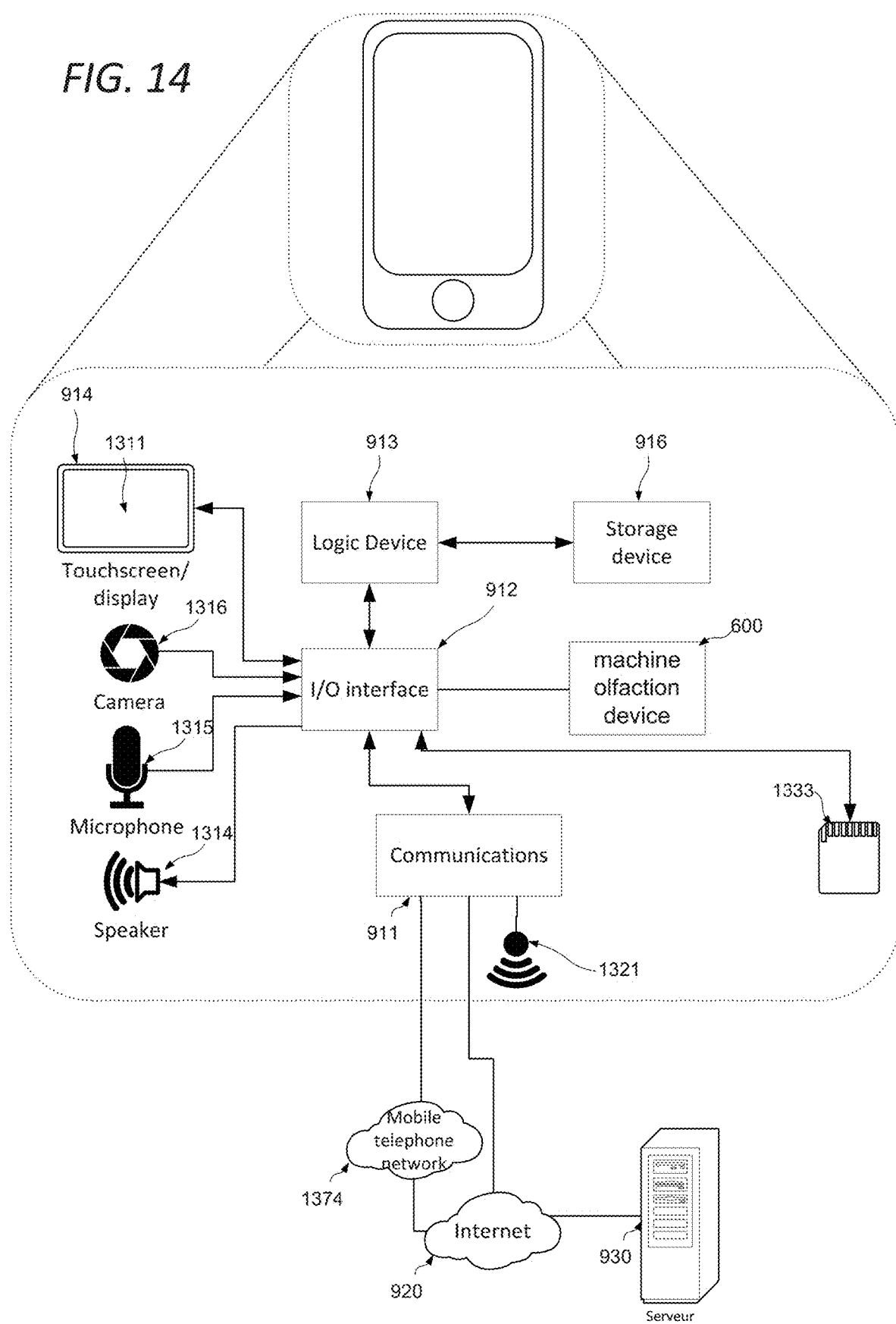
FIG. 14 shows a smartphone device adaptable to constitute an embodiment.
Figure 15:
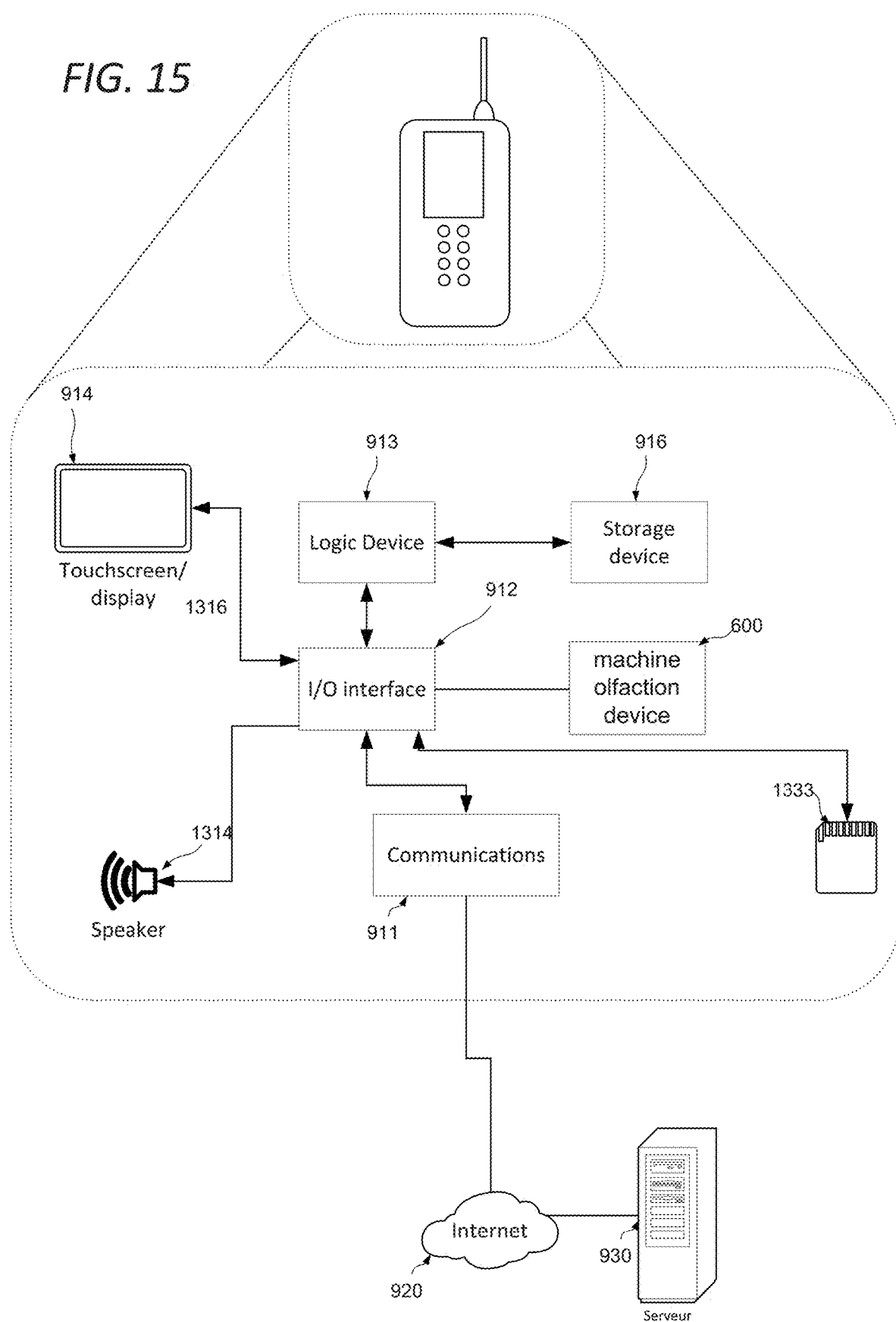
FIG. 15 shows a hand scanner device adaptable to constitute an embodiment.
Figure 16:
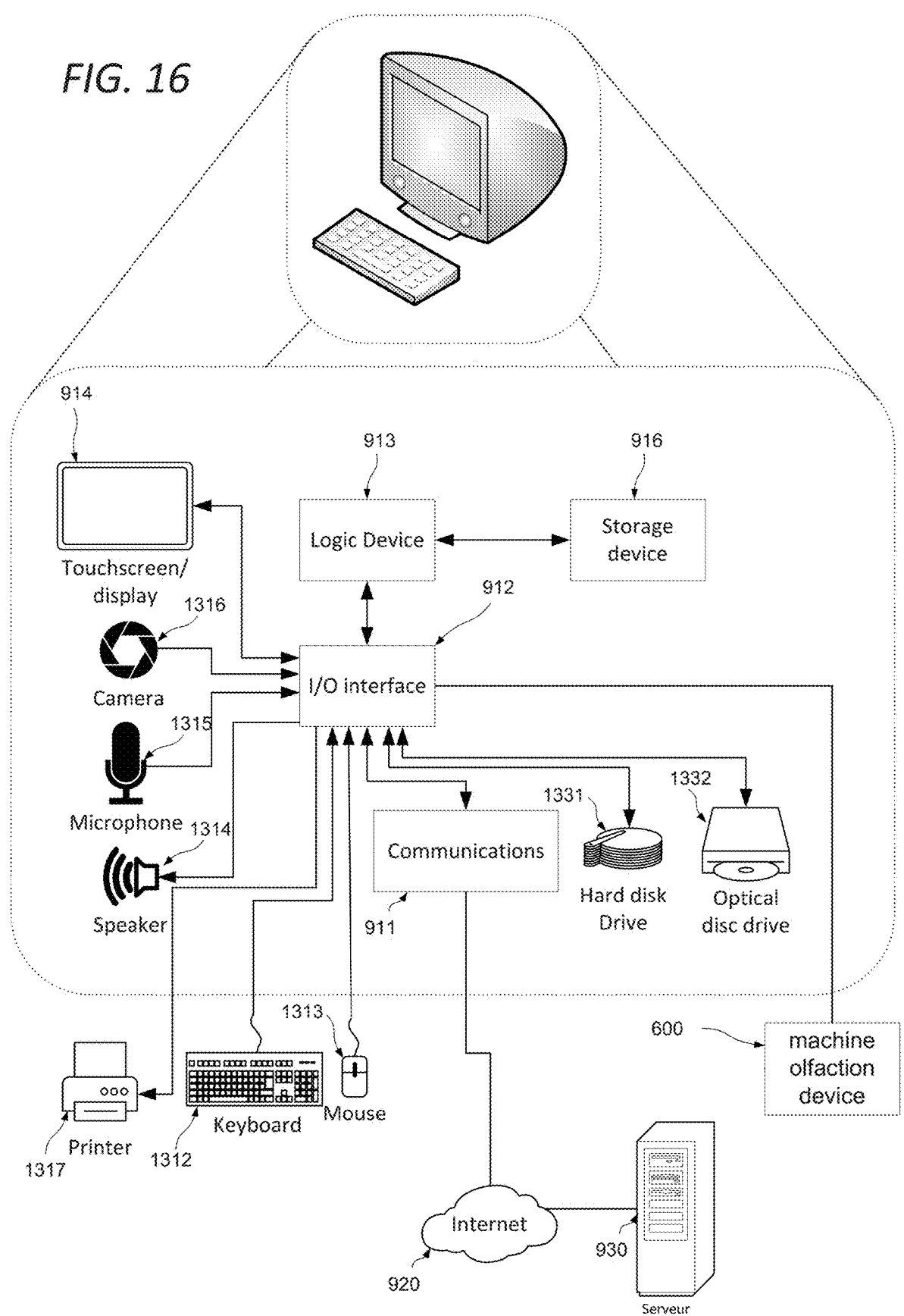
FIG. 16 shows a desktop computer device adaptable to constitute an embodiment.

The system of FIG. 13 is intended to reflect a broad range of different types of information handling system. It will be appreciated that many of the subsystems and features described with respect to FIG. 13 are not required for implementation of the invention, but are included to more realistically reflect common systems. It will be appreciated that system architectures vary widely, and the relationship between the different sub-systems of FIG. 13 is merely schematic, and is likely to vary in terms of layout and the distribution of roles in real systems. It will be appreciated that in practice, systems are likely to incorporate different subsets of the various features and subsystems described with respect to FIG. 13. FIGS. 14, 15 and 16 discuss in further detail some common example devices.

FIG. 14 shows a smartphone device adaptable to constitute an embodiment. As shown in FIG. 14, the smartphone device incorporates elements 914, 913, 916, 912, 600, 1316, 1315, 1314, 911, 1321 and 1333 as described above. It is in communication with the telephone network 1374 and a server 930 via the network 920.

FIG. 15 shows a hand scanner device adaptable to constitute an embodiment. As shown in FIG. 15, the hand scanner device incorporates elements 914, 913, 916, 912, 600, 1314, 911, 1333, 920 and 930 as described above. It is in communication with a server 930 via the network 920.

FIG. 16 shows a desktop computer device adaptable to constitute an embodiment. As shown in FIG. 16, the desktop computer device incorporates elements 914, 913, 916, 912, 600, 1314, 911, 1333, 920 and 930 as described above. It is in communication with elements 1317, 1312, 1313 and 600 as peripheral devices, and with a server 930 via the network 920. On the other hand, elements 1321, 1374 and 1333 are omitted, and element 914 may be an ordinary display with no touchscreen functionality.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A system for characterizing a gas sample, said system comprising a gas sensor, a controller and a memory, wherein said controller is adapted to identify a sample type of said gas sample, and to modify two or more operating conditions of said gas sensor during a measurement cycle in accordance with a measurement protocol corresponding to said sample type, and determining at what times during said measurement cycle readings should be taken, and what values should be set for said first operating condition and said second operating condition to discriminate most clearly between target characterizations corresponding to said sample type, said measurement cycle starting with an initial reading from said gas sensor and ending with a final reading from said gas sensor, and comprising a plurality of measurements sufficient for said characterization, and wherein said controller is further adapted to compare the readings received from said gas sensor throughout said measurement cycle with a plurality of target characterizations stored in said memory, each said target characterization being associated with a respective category, and classifying said gas sample in the category of whichever candidate measured characterizations most closely matches said readings.

2. The system of claim 1 wherein said controller is adapted to modify the first and second operating conditions to values specified in said measurement protocol.

3. The system of claim 2 wherein said controller is adapted to initiate said measurement cycle, to modify said two or more operating conditions and to record said measurements at times specified in said measurement protocol.

4. The system of claim 1 wherein said system further comprises a communications interface, permitting communication with a remote processor, and wherein said controller is further adapted to transmit the readings received from said gas sensor throughout said measurement cycle to said remote processor for comparison with a plurality of candidate measured characterizations.

5. The system of claim 1 wherein said system comprises an ultra violet light source arranged so as to illuminate a reactive surface of said gas sensor, said ultra violet light source coupled to said controller such that said controller can select an intensity or a wavelength of said light source, and wherein the intensity of said light source is one of the operating conditions of the gas sensor.

6. The system of claim 1 wherein said system comprises a heat source arranged so as to heat a reactive surface of said gas sensor, said heat source coupled to said controller such that said controller can modulate an intensity of said heat source, and wherein the intensity of said heat source is one of the operating conditions of the gas sensor.

7. The system of claim 1 wherein said system comprises a voltage source powering said gas sensor, said voltage source coupled to said controller such that said controller can modulate the voltage output of said voltage source, and wherein the voltage of said voltage source is one of the operating conditions of the gas sensor.

8. The system of claim 1 wherein said system comprises a chemical filter situated so as to control access of said gas sample to said gas sensor, said chemical filter comprising a heater coupled to said controller such that said controller can modulate a temperature of output of said chemical filter, and wherein the temperature of said chemical filter is one of the operating conditions of the gas sensor.

9. A method of characterizing a gas sample, said method comprising steps of identifying a sample type of said gas sample, setting initial operating conditions for a gas sensor, initiating a measurement cycle by taking a first reading from said gas sensor, modifying a first specified operating condition of said gas sensor at a first predefined time, modifying a second specified operating condition of said gas sensor at a second predefined time, and terminating said measurement cycle with a final reading from said gas sensor, wherein said steps are defined in a measurement protocol corresponding to said sample type and determining at what times during said measurement cycle readings should be taken, and what values should be set for said first specified operating condition and said second specified operating condition to discriminate most clearly between target characterizations corresponding to said sample type, and comparing said readings from said gas sensor with a plurality of target characterizations, each said target characterization being associated with a respective category, and classifying said gas in the category of whichever candidate measured characterizations most closely matches said readings.

10. The method of claim 9 comprising the further steps of transmitting said the readings to a remote processor for comparison with a plurality of candidate measured characterizations, and receiving said characterization from said remote processor.

11. The method of claim 9 further comprising generating said measurement protocol to determine at what times during a measurement cycle readings should be taken, and what values should be set for said first operating condition and said second operating condition to discriminate most clearly between said target characterizations.

12. A method of generating a measurement protocol for use in claim 9, said method comprising determining at what times during a measurement cycle readings should be taken, and what values should be set for said first operating condition and said second operating condition to discriminate most clearly between said target characterizations by applying sequentially all combinations of different operating conditions corresponding to those that the final measurement system is able to modulate to a set of representative samples, and applying a multivariate analysis technique to a resulting matrix.

13. A computer readable non-transitory storage medium having computing instructions stored therein, wherein the computing instructions when executed by one or more processor implement the method of claim 9.

* * * * *